United States Patent
Livoreil et al.

(10) Patent No.: US 6,726,915 B2
(45) Date of Patent: Apr. 27, 2004

(54) COSMETIC OR PHARMACEUTICAL COMPOSITION IN SOLID FORM COMPRISING BIS-ACYL-AMIDES

(75) Inventors: Aude Livoreil, Paris (FR); Sylvie Genard, Nogent sur Marne (FR)

(73) Assignee: L'Oreal, Paris (FR)

( * ) Notice: Subject to any disclaimer, the term of this patent is extended or adjusted under 35 U.S.C. 154(b) by 147 days.

(21) Appl. No.: 10/088,296
(22) PCT Filed: Jul. 16, 2001
(86) PCT No.: PCT/FR01/02306
§ 371 (c)(1),
(2), (4) Date: Apr. 10, 2002
(87) PCT Pub. No.: WO02/05763
PCT Pub. Date: Jan. 24, 2002

(65) Prior Publication Data
US 2003/0129211 A9 Jul. 10, 2003

(30) Foreign Application Priority Data
Jul. 17, 2000 (FR) ............................................. 00 09317

(51) Int. Cl.⁷ ..................... A61K 6/00; A61K 7/00; A61K 7/025; A61K 7/06; A61K 7/42
(52) U.S. Cl. .................. 424/400; 424/64; 424/70.1; 424/70.7; 424/47; 424/59
(58) Field of Search ..................... 424/400, 70.1, 424/64, 401, 70.7, 47, 59

(56) References Cited
U.S. PATENT DOCUMENTS 3,857,960 A     12/1974    Mackles
5,705,148 A  *  1/1998    Bollens et al. ............. 424/70.1

FOREIGN PATENT DOCUMENTS

JP     7-138555      5/1995
JP     10-237034     9/1998

OTHER PUBLICATIONS

Kenji Hanabusa et al., "Prominent Gelation and Chiral Aggregation of Alkylamides Derived from trans–1,2–Diaminocyclohexane," Angewandte Chemie, International Addition in English, vol. 35, No. 17, 1996, pp. 1949–1951.

English language Derwent Abstract of JP 10–237034, Sep. 8, 1998.

English language Derwent Abstract of JP 7–138555, May 30, 1995.

* cited by examiner

Primary Examiner—Thurman K. Page
Assistant Examiner—S. Howard
(74) Attorney, Agent, or Firm—Finnegan Henderson Farabow Garrett & Dunner, L.L.P.

(57) ABSTRACT

The present application relates to a composition, in particular a cosmetic or pharmaceutical composition, which is in solid form, comprising an oily phase and at least one compound of formula (I) below:

R—CO—NH—A—NH—CO—R' in which R and R' represent a hydrogen atom or a hydrocarbon-based chain; and A represents a hydrocarbon-based chain.

93 Claims, No Drawings

COSMETIC OR PHARMACEUTICAL COMPOSITION IN SOLID FORM COMPRISING BIS-ACYL-AMIDES

The present invention relates to a solid composition, in particular a solid cosmetic or pharmaceutical composition, such as a care, treatment and/or make-up composition for the skin, including the scalp, and/or for the lips of human beings, the said composition comprising a thickened liquid fatty phase and being in particular in the form of a stick or tube of make-up, such as a lipstick.

It is common practice to use a structured, i.e. thickened or gelled, liquid fatty phase in compositions, in particular cosmetic and dermatological compositions, in order to obtain the desired consistency. The thickening of oils (or of phases that are liquid at room temperature) in particular makes it easier to take up the product from its packaging without any significant loss, to limit the diffusion of the product to the local treatment area, to distribute the product uniformly over the local treatment area or to be able to use the product in amounts that are sufficient to obtain the desired cosmetic or dermatological effect. This is especially the case in solid compositions such as deodorants, lip balms and lipsticks, concealer products and cast foundations. This thickening is of prime importance in particular for care, hygiene or make-up compositions such as lipsticks which need to be distributed homogeneously over the local surface to be treated, as well as for hair compositions which need to be spread and distributed uniformly along the keratin fibres and not run down the forehead, the nape of the neck, the face or into the eyes.

To overcome these problems, use is usually made of waxes or fillers. Unfortunately, these waxes and/or fillers have a tendency to make the composition matt and opaque, which is not always desirable, in particular for a lipstick. Specifically, women are always in search of a lipstick in the form of a tube which gives a glossy film; moreover, certain compositions such as lip balms or ointments can be in the form of translucent, or even transparent, sticks.

It is also known practice to thicken oils with polymeric thickeners. Unfortunately, the known thickeners for oils have to be used in large amounts in order to obtain a gel of high viscosity, for example of greater than 1.3 Pa.s. However, too large an amount of thickener can give the composition inadequate cosmetic properties, in particular a sticky feel and a lack of slipperiness, these drawbacks potentially being very inconvenient, or even unacceptable.

Moreover, it is also known practice to gel compositions, in particular cosmetic compositions, using a gelling agent of trialkyl tri(alkylamino-carbonyl)cyclohexane type. These gelling agents make it possible to improve the stability of the compositions comprising them. However, once again, the gels obtained have poor transparency. Furthermore, a large proportion of these gelling agents do not allow oily silicone media to be gelled.

Finally, it is known practice to thicken cosmetic compositions with diamide derivatives, especially in documents JP7/138 555 and JP10/237 034. However, the cosmetic compositions disclosed in the said prior art all comprise a large amount of waxes (beeswax, ozokerite or hexadecanoic acid in particular). The structuring and gelation of the stick therefore does not take place solely due to the diamide compounds, but also due to the waxes. However, using a large amount of waxes has certain drawbacks, especially in terms of the matt effect or opacity of the final composition thus prepared.

Furthermore, it is not possible to incorporate silicone oils in large amount into a composition also comprising conventional waxes.

One object of the present invention is to propose the production of a composition, in particular a cosmetic composition, which is in solid form, and which preferably comprises little or even no waxes, while at the same time being capable, firstly, of retaining good cosmetic properties, and in particular a certain level of translucency, or even transparency, and, secondly, of comprising silicone oils, in particular in large amount.

One subject of the invention is thus a composition, in particular a cosmetic or pharmaceutical composition, which is in solid form, comprising an oily phase and at least one compound of formula (I) below:

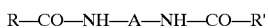

in which:

R and R', which may be identical or different, represent a hydrogen atom or a saturated or unsaturated, linear, branched or cyclic, preferably a saturated linear, hydrocarbon-based chain containing from 1 to 22 carbon atoms, in particular 6–18 carbon atoms, preferably from 10 to 14 carbon atoms, more preferably from 11 to 13 carbon atoms and better still 11 carbon atoms, optionally substituted with one or more groups chosen from aryl (—$C_6H_5$) ester (—COOR" with R" being an alkyl group containing 2 to 12 carbon atoms), amide (—CONHR" with R" being an alkyl group containing 2 to 12 carbon atoms), urethane (—OCONHR" with R" being an alkyl group containing 2 to 12 carbon atoms) and urea (—NHCONHR" with R" being an alkyl group containing 2 to 12 carbon atoms) groups; and/or optionally containing 1 to 3 hetero atoms chosen from O, S and N; and/or optionally substituted with 1 to 4 halogen atoms, in particular fluorine atoms, and/or with 1 to 3 hydroxyl radicals, on condition that R and R' are other than hydrogen, and A represents a saturated or unsaturated, linear, cyclic or branched hydrocarbon-based chain (in the form of a divalent radical) containing 1 to 18 carbon atoms, in particular 2 to 12 carbon atoms and preferably from 4 to 10 carbon atoms, optionally substituted with one or more groups chosen from aryl (—$C_6H_5$), ester (—COOR" with R" being an alkyl group containing 2 to 12 carbon atoms), amide (—CONHR" with R" being an alkyl group containing 2 to 12 carbon atoms), urethane (—OCONHR" with R" being an alkyl group containing 2 to 12 carbon atoms) and urea (—NHCONHR" with R" being an alkyl group containing 2 to 12 carbon atoms) groups; and/or optionally containing 1 to 3 hetero atoms chosen from O, S and N; and/or optionally substituted with 1 to 4 halogen atoms, in particular fluorine atoms, and/or with 1 to 3 hydroxyl radicals.

Specifically, it is been found that using the compounds of formula (I) makes it possible to structure and thicken liquid (or oily) fatty phases substantially, or even to gel them completely, and thus to obtain stable cosmetic compositions in solid gelled form, which have satisfactory cosmetic properties. These compositions may even be free of waxes while at the same time retaining their rigidity and their good cosmetic properties. Moreover, the liquid fatty phase may be gelled even though it comprises a large amount of silicone oils.

The composition according to the invention has good cosmetic properties: it is not sticky when applied and is slippery and easy to apply. It produces a homogeneous, uniform film which covers well and is comfortable to wear.

Furthermore, the composition may advantageously be clear, transparent or translucent. These terms are understood as having their conventional dictionary definitions. Thus, a translucent composition allows light to pass through without, however, allowing the contours of objects to be clearly distinguished. A transparent composition allows light to pass through easily and allows objects to be distinguished clearly through its thickness.

In general, a transparent composition will have a maximum light transmittance value, irrespective of the wavelength, of between 400 nm and 800 nm, through a 1 cm thick sample, of between 35% and 100% and preferably of at least 50% (see EP 291 334). A translucent composition will have a maximum light transmittance value of between 2% and 35%. The transmittance can be measured by placing a 1 cm thick sample in the light beam of a spectrophotometer working in the wavelengths of the light spectrum.

The composition according to the invention thus comprises at least one compound corresponding to formula (I) below:

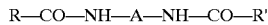

R—CO—NH—A—NH—CO—R' in which:

R and R', which may be identical or different, represent a hydrogen atom or a saturated or unsaturated, linear, branched or cyclic, preferably a saturated linear, hydrocarbon-based chain containing from 1 to 22 carbon atoms, in particular 6–18 carbon atoms, preferably from 10 to 14 carbon atoms, more preferably from 11 to 13 carbon atoms and better still 11 carbon atoms, optionally substituted with one or more groups chosen from aryl (—$C_6H_5$), ester (—COOR" with R" being an alkyl group containing 2 to 12 carbon atoms), amide (—CONHR" with R" being an alkyl group containing 2 to 12 carbon atoms), urethane (—OCONHR" with R" being an alkyl group containing 2 to 12 carbon atoms) and urea (—NHCONHR" with R" being an alkyl group containing 2 to 12 carbon atoms) groups; and/or optionally containing 1 to 3 hetero atoms chosen from O, S and N; and/or optionally substituted with 1 to 4 halogen atoms, in particular fluorine atoms, and/or with 1 to 3 hydroxyl radicals, on condition that R and R' are other than hydrogen, and A represents a saturated or unsaturated, linear, cyclic or branched hydrocarbon-based chain (in the form of a divalent radical) containing 1 to 18 carbon atoms, in particular 2 to 12 carbon atoms and preferably from 4 to 10 carbon atoms, optionally substituted with one or more groups chosen from aryl (—$C_6H_5$), ester (—COOR" with R" being an alkyl group containing 2 to 12 carbon atoms), amide (—CONHR" with R" being an alkyl group containing 2 to 12 carbon atoms), urethane (—OCONHR" with R" being an alkyl group containing 2 to 12 carbon atoms) and urea (—NHCONHR" with R" being an alkyl group containing 2 to 12 carbon atoms) groups; and/or optionally containing 1 to 3 hetero atoms chosen from O, S and N; and/or optionally substituted with 1 to 4 halogen atoms, in particular fluorine atoms, and/or with 1 to 3 hydroxyl radicals.

The expression "unsaturated hydrocarbon-based chain" means a chain which comprises at least one C=C double bond or at least one C•C triple bond, it being possible, needless to say, for the said chain also to be optionally substituted with one or more groups chosen from aryl, ester, amide, urethane and urea groups; and/or optionally to comprise one or more hetero atoms chosen from O, S and N; and/or to be optionally substituted with one or more fluorine atoms and/or hydroxyl radicals.

The expression "hydrocarbon-based chain comprising an oxygen, sulphur or nitrogen atom" means in particular a hydrocarbon-based chain comprising a carbonyl (—C=O), amine (—$NH_2$ or —NH—), thiol (—SH), thio ether or ether group.

Advantageously, A represents a divalent radical with a saturated cyclic hydrocarbon-based chain containing from 4 to 10 carbon atoms.

According to one preferred embodiment of the composition according to the invention, the radicals R and R' of the compounds of formula (I) are identical.

The compounds preferably correspond to formula (I) in which:

1/
A represents a saturated or unsaturated, preferably saturated, but non-aromatic, optionally branched hydrocarbon-based ring (in the form of a divalent radical) containing from 4 to 12 carbon atoms, in particular from 5 to 7 carbon atoms, optionally substituted with the substituents mentioned above and/or optionally comprising one or more hetero atoms and/or optionally substituted with one or more halogens and/or hydroxyl radicals;

R and R', which may be identical or different, represent a hydrogen atom or a saturated or unsaturated, linear, branched or cyclic, preferably a saturated linear, hydrocarbon-based chain containing from 10 to 16 carbon atoms, in particular 10 to 14 carbon atoms or even from 12 to 14 carbon atoms and better still 11 carbon atoms, on condition that R and R' are other than hydrogen, 2/
A represents a saturated, linear or branched hydrocarbon-based chain (in the form of a divalent radical) containing from 2 to 18 carbon atoms, in particular from 3 to 12 carbon atoms, optionally substituted with the substituents mentioned above, and/or optionally comprising one or more hetero atoms and/or optionally substituted with one or more halogens and/or hydroxyl radicals;

R and R', which may be identical or different, represent a hydrogen atom or a saturated or unsaturated, linear, branched, or cyclic hydrocarbon-based chain, preferably a saturated linear hydrocarbon-based chain, containing from 10 to 20 carbon atoms, in particular from 11 to 18 carbon atoms, preferably from 11 to 13 carbon atoms and better still 11 carbon atoms, on condition that R and R' are other than hydrogen, or alternatively 3/
A represents an aryl or aralkyl ring (in the form of a divalent radical) containing from 6 to 12 carbon atoms, in particular from 6 to 8 carbon atoms, optionally substituted with the substituents mentioned above and/or optionally comprising one or more hetero atoms and/or optionally substituted with one or more halogens and/or hydroxyl radicals;

R and R', which may be identical or different, represent a hydrogen atom or a saturated or unsaturated, linear, branched or cyclic hydrocarbon-based chain, preferably a saturated linear hydrocarbon-based chain, containing from 6 to 18 carbon atoms, in particular from 10 to 16 carbon atoms, preferably comprising from 11 to 13 carbon atoms and more preferably containing 11 carbon atoms, on condition that R and R' are other than hydrogen.

In particular, the radical A can represent a divalent radical of cyclohexylene (in particular 1,2-cyclohexylene, 1,3-cyclohexylene, 1,4-cyclohexylene, preferably 1,2-cyclohexylene), ethylene, propylene, isopropylene, butylene, isobutylene, pentylene, hexylene, dodecylene, dodecanylene, benzylene, phenylene, methylphenylene, bisphenylene or naphthalene type; preferably A may be a divalent radical of cyclohexylene, ethylene, propylene, isopropylene, dodecylene or methylphenylene type.

The radicals R and R' may be chosen, independently of each other, from pentyl, hexyl, decyl, undecyl, dodecyl, pentadecyl, hexadecyl, heptadecyl, octadecyl, 3-dodecyloxypropionyl, 3-octadecyloxypropionyl, 3-dodecyloxypentyl, 3-octadecyloxypentyl and 11-hydroxyheptadecyl radicals. Preferably, R and R' may be chosen, independently of each other, from decyl, undecyl and dodecyl radicals. R and R' are advantageously identical.

When the radical A is cyclic and in particular is a cyclohexylene, the radicals R—CO—NH— and R'—CO—NH— may be in an ortho, meta or para position; moreover, these radicals may be in a cis or trans position relative to each other. The compound of formula (I) may moreover comprise a mixture of the cis compound and of the trans compounds (racemic mixture or 1R, 2R or 1S, 2S enantiomers, or mixtures thereof in variable proportion). The stereochemistry of the compound of formula (I) in fact corresponds to the stereochemistry of the diamine of formula $H_2N-A-NH_2$ used during the preparation of the compounds, which preparation is described below.

The compounds of formula (I) are preferably chosen from the compounds corresponding to one of the following formulae:

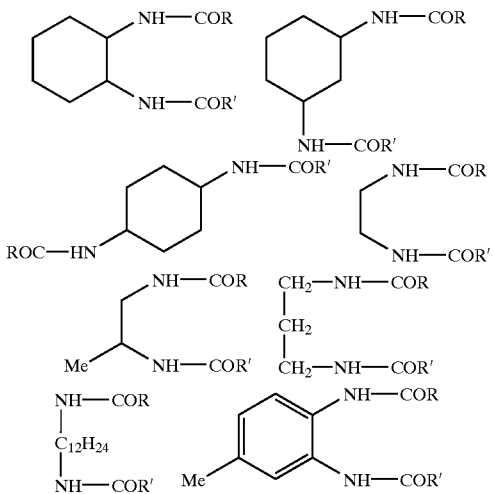

in which R and R' have the same meanings as above.

Among the compounds which may be used in the context of the invention, mention may be made of:

N,N'-bis(dodecanoyl)-1,2-diaminocyclohexane, in particular in trans form (compound of formula (I) with R=R'=n-$C_{11}H_{23}$ and A=1,2-cyclohexylene divalent radical, also known as (2-dodecanoylaminocyclohexyl)-dodecanamide. This compound is described in particular in Hanabusa, K; Angew. Chem., 108, 1997, 17, pages 2086–2088

N,N'-bis(dodecanoyl)-1,3-diaminocyclohexane, in particular in trans form (compound of formula (I) with R=R'=n-$C_{11}H_{23}$ and A=1,3-cyclohexylene divalent radical, also known as (3-dodecanoylaminocyclohexyl) dodecanamide N,N'-bis(dodecanoyl)-1,4-diaminocyclohexane, in particular in trans form (compound of formula (I) with R=R'=n-$C_{11}H_{23}$ and A=1,4-cyclohexylene divalent radical, also known as (4-dodecanoylaminocyclohexyl)-dodecanamide)

N,N'-bis(dodecanoyl)-1,2-ethylenediamine (compound of formula (I) with R=R'=n-$C_{11}H_{23}$ and A=1,2-ethylene divalent radical, also known as (2-dodecanoylaminoethyl)dodecanamide)

N,N'-bis(dodecanoyl)-1-methyl-1,2-ethylenediamine (compound of formula (I) with R=R'=n-$C_{11}H_{23}$ and A=1-methyl-1,2-ethylene divalent radical, also known as (2-dodecanoylamino-2-methylethyl)dodecanamide)

N,N'-bis(dodecanoyl)-1,3-diaminopropane (compound of formula (I) with R=R'=n-$C_{11}H_{23}$ and A=1,3-propylene divalent radical, also known as (2-dodecanoylaminopropyl)dodecanamide)

N,N'-bis(dodecanoyl)-1,12-diaminododecane (compound of formula (I) with R=R'=n-$C_{11}H_{23}$ and A=1,12-dodecylene divalent radical, also known as (2-dodecanoylaminododecyl)dodecanamide)

N,N'-bis(dodecanoyl)-3,4-diaminotoluene (compound of formula (I) with R=R'=n-$C_{11}H_{23}$ and A=1-methyl-3,4-phenylene divalent radical, also known as (2-dodecanoylamino-4-methylphenyl)dodecanamide).

The compounds of formula (I) can be prepared according to processes that are well known to those skilled in the art.

In particular, they may be obtained by reacting a diamine $H_2N-A-NH_2$ with an acid chloride RCOCl and/or R'COCl with R and R' having the above meaning, but other than a hydrogen atom, in an organic solvent medium which is compatible for carrying out the reaction (1 mol of acid chloride is used per 1 mol of diamine if it is desired to obtain a compound of formula (I) containing only one group R other than a hydrogen atom, or 2 mol of acid chloride RCOCl and/or R'COCl if it is desired to obtain a compound of formula (II) with R and R' other than a hydrogen atom). The reaction is preferably carried out in the presence of a base capable of neutralizing the formation of the HCl released during the reaction. The diamide formed is extracted from the reaction medium according to the conventional extraction techniques that are well known to those skilled in the art.

The compound of formula (I) is preferably present in the composition in an amount which may readily be determined by a person skilled in the art depending on the desired effect, and which may be between 1% and 40% by weight, for example between 2% and 15% by weight, relative to the total weight of the composition, and better still between 4% and 12% by weight, or even between 5% and 10% by weight.

It has moreover been observed that even the use of a small amount of compounds of formula (I), for example about 2–6% by weight, can lead to an adequate gelation of the composition according to the invention. This is due to the high thickening power of the compounds of formula I, which enables them to be effective at low concentration, of about 4–8% by weight, whereas it would be necessary to use 10–20% by weight of common gelling agents in order to obtain an equivalent result.

Without being bound by the present explanation, it has been observed that the structuring, or gelation, of oils by means of the compounds of formula (I) may be due to the formation of piles in the form of columns of the molecules of compounds of formula (I), resulting in the formation of a network of fibres or lamellae, consisting of the said compounds of formula (I) and the oils, the said network not scattering light, resulting in a certain level of translucency, or even transparency.

The compounds of formula (I) can be used in particular, alone or as a mixture, in a composition which comprises a physiologically acceptable medium, in particular in a cosmetic composition which thus moreover comprises a cosmetically acceptable medium.

This physiologically acceptable medium, its constituents, their amount, the pharmaceutical form of the composition and the method for preparing it, may be chosen by a person skilled in the art on the basis of his general knowledge depending on the type of composition desired.

Generally, the composition according to the invention comprises, in an oily phase, at least one cosmetically or dermatologically acceptable oil, a fatty substance which is liquid at room temperature (25° C.).

These oils can be hydrocarbon-based oils and/or silicone oils and/or fluoro oils. They can be of animal, plant, mineral or synthetic origin.

Mention may be made in particular of:

hydrocarbon-based oils of animal origin such as perhydrosqualene;

hydrocarbon-based plant oils such as liquid triglycerides of fatty acids of 4 to 10 carbon atoms, for instance heptanoic or octanoic acid triglycerides; sunflower oil, corn oil, soybean oil, marrow oil, grapeseed oil, groundnut oil, sweet almond oil, beauty-leaf oil, palm oil, sesame oil, hazelnut oil, apricot oil, macadamia oil, castor oil, avocado oil; caprylic/capric acid triglycerides, for instance those sold by the company Stearineries Dubois or those sold under the names Miglyol 810, 812 and 818 by the company Dynamit Nobel; jojoba oil, karite butter;

linear or branched hydrocarbons of mineral or synthetic origin, such as liquid paraffins and derivatives thereof, petroleum jelly, polydecenes, and hydrogenated polyisobutene such as parleam;

synthetic esters and ethers, in particular of fatty acids, for instance the oils of formula $R_3COOR_4$ in which $R_3$ represents a higher fatty acid residue containing from 7 to 29 carbon atoms and $R_4$ represents a hydrocarbon-based chain containing from 3 to 30 carbon atoms, such as, for example, purcellin oil (cetostearyl ocatanoate), isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate or diethylene glycol diisononanoate; and pentaerythritol esters; tridecyl trimellitate;

fatty alcohols containing from 12 to 26 carbon atoms, for instance octyldodecanol, 2-butyloctanol, 2-hexyldecanol, 2-undecylpentadecanol or oleyl alcohol;

partially hydrocarbon-based and/or silicone-containing fluoro oils;

silicone oils, for instance volatile or non-volatile, linear or cyclic polymethylsiloxanes (PDMSs); alkyldimethicones; silicones modified with aliphatic and/or aromatic groups, which are optionally fluorinated, or with functional groups such as hydroxyl, thiol and/or amine groups; phenylsilicone oils such as polyphenylmethylsiloxanes or phenyltrimethicones;

mixtures thereof.

The oils used can be volatile and/or non-volatile. The term "volatile oil" means an oil which is capable of evaporating at room temperature from a support onto which it has been applied, in other words an oil which has a measurable vapour pressure at 25° C. and 1 atmosphere, for example greater than 0 Pa, in particular ranging from $10^{-3}$ mmHg to 300 mmHg (0.13 Pa to 40,000 Pa).

Mention may be made in particular of volatile silicone oils, such as volatile cyclic or linear silicones, and cyclocopolymers. Mention may also be made of volatile hydrocarbon-based oils such as isoparaffins, and volatile fluoro oils.

In one specific embodiment, the volatile oils can constitute the majority of the oily phase. Thus, they can be present therein in a proportion of at least 50% by weight, in particular at least 75% by weight, or even 100% by weight, of the said oily phase.

In another preferred embodiment, the oily phase may comprise silicone oils, in particular in a large amount of about 40–80% by weight of the oily phase, in particular of about 60–75% by weight; the oily phase may also comprise 100% by weight of silicone oil, while at the same time remaining entirely stable and solid.

The oils can be present in the composition in a proportion of from 5% to 99% by weight relative to the total weight of the composition, preferably from 20% to 75% by weight.

The composition according to the invention is preferably in solid form. This means that, in the absence of mechanical or thermal stimulation (in particular heating), no collapse of the composition is observed when it is outside the container containing it.

The composition has the conventional viscoelastic behaviour of a composition of solid type.

Moreover, the hardness of the composition according to the invention is preferably such that the composition is self-supporting and can disintegrate readily to form a satisfactory deposit on the skin and the lips. This hardness can be between 0.04 N and 3 N, preferably between 0.1 N and 2.5 N and in particular between 0.2 N and 2 N. This hardness can be measured according to a method of penetration of a probe into the said composition and in particular using a texture analyser (for example TA-XT2 from Rheo) equipped with an acrylic cone with an apex angle of 45°. The hardness measurement is carried out at 22° C. at the centre of 5 samples of the said composition, according to the method described in the examples.

This composition advantageously comprises little or even no wax, while at the same time retaining adequate solidity/rigidity/hardness. This means that the composition comprises less than about 5% by weight of wax, relative to the total weight of the composition, preferably less than 2% by weight, or even less than 0.5% by weight, of wax. The composition preferentially contains no waxes (i.e. 0%).

For the purposes of the present invention, a wax is a lipophilic fatty compound, which is solid at room temperature (about 25° C.), undergoes a reversible solid/liquid change of state, has a melting point of greater than about 40° C. which may be up to 200° C., and has an anisotropic crystal organization in the solid state.

For the purpose of the present application, the waxes are those generally used in the cosmetic and pharmaceutical fields.

They are, in particular, natural waxes of animal, plant or mineral origin, such as beeswax, montan wax, carnauba wax, candelilla wax, China wax, flax wax, pine wax, cotton wax, ouricury wax, lignite wax, rice bran wax, sugar cane wax, Japan wax or cork fibre wax.

Mention may also be made of paraffin waxes, microcrystalline waxes, lanolin wax, ozokerites, hydrogenated oils with a melting point of greater than about 40° C., for instance hydrogenated jojoba oil, polyethylene waxes derived from the polymerization of ethylene, waxes obtained by Fischer-Tropsch synthesis, fatty acid esters and glycerides with a melting point of greater than about 40° C., and silicone waxes, for instance alkyl, alkoxy and/or esters of poly(di)methylsiloxane that are solid at 40° C.

The composition according to the invention can moreover comprise the constituents usually used in the type of application envisaged.

It can comprise one or more organic solvents chosen in particular from:

- ketones that are liquid at room temperature, such as methyl ethyl ketone, methyl isobutyl ketone, diisobutyl ketone, isophorone, cyclohexanone or acetone;
- alcohols that are liquid at room temperature, such as ethanol, isopropanol, diacetone alcohol, 2-butoxyethanol or cyclohexanol;
- glycols that are liquid at room temperature, such as ethylene glycol, propylene glycol or pentylene glycol;
- propylene glycol ethers that are liquid at room temperature, such as propylene glycol monomethyl ether, propylene glycol monomethyl ether acetate or dipropylene glycol mono-n-butyl ether;
- short-chain esters (containing from 3 to 8 carbon atoms in total) such as ethyl acetate, methyl acetate, propyl acetate, n-butyl acetate or isopentyl acetate;
- ethers that are liquid at room temperature, such as diethyl ether, dimethyl ether or dichlorodiethyl ether;
- alkanes that are liquid at room temperature, such as decane, heptane, dodecane or cyclohexane;
- cyclic aromatic compounds that are liquid at room temperature, such as toluene and xylene;
- aldehydes that are liquid at room temperature, such as benzaldehyde and acetaldehyde.

It is also possible to incorporate a hydrophilic phase into the composition according to the invention, in particular in an amount of 0–10% by weight relative to the total weight of the composition, and better still 1–5% by weight, which can comprise hydrophilic active agents and/or hydrophilic gelling agents. It can in particular comprise moisturizers such as glycerol.

The composition advantageously comprises a dyestuff which can be chosen from the lipophilic dyes, hydrophilic dyes, pigments and nacres usually used in cosmetic or dermatological compositions, and mixtures thereof. This dyestuff is generally present in a proportion of from 0.01% to 40% relative to the total weight of the composition, preferably from 5% to 25% by weight.

Thus, the composition can comprise a particulate phase, which is generally present in a proportion of 0–30% by weight, preferably 0–20% by weight, and which can comprise pigments and/or nacres and/or fillers usually used in cosmetic compositions. The term "pigments" should be understood as meaning white or coloured, mineral or organic particles intended to colour and/or opacify the composition. The term "fillers" should be understood as meaning colourless or white, mineral or synthetic, lamellar or non-lamellar particles intended to give body or rigidity to the composition, and/or softness, a matt effect and uniformity to the make-up result. The term "nacres" should be understood as meaning iridescent particles which reflect light.

The pigments can be white or coloured, mineral and/or organic, of micrometric or nanometric size. Mineral pigments which may be mentioned include titanium dioxide, zirconium dioxide or cerium dioxide, and also zinc oxide, iron oxide or chromium oxide and ferric blue. Organic pigments which may be mentioned include carbon black and barium, strontium, calcium and aluminium lakes.

Among the nacres which may be envisaged, mention may be made of mica coated with titanium oxide, with iron oxide, with natural pigment or with bismuth oxychloride, and also coloured titanium mica.

The fillers can be mineral or synthetic, and lamellar or non-lamellar. Mention may be made of talc, mica, silica, kaolin, Nylon powder, polyethylene powder, Teflon, starch, titanium mica, natural mother-of-pearl, boron nitride, microspheres such as Expancel (Nobel Industrie), Polytrap (Dow Corning) and silicone resin microbeads (Tospearls from Toshiba, for example).

The composition according to the invention can also comprise any additive usually used in the field under consideration, in particular in cosmetics, such as antioxidants, fragrances, dyes, essential oils, preserving agents, cosmetic active agents, vitamins, essential fatty acids, sphingolipids, self-tanning compounds such as DHA, sunscreens, surfactants and polymers. These additives can be present in the composition in a proportion of 0–10% by weight.

Needless to say, a person skilled in the art will take care to select this or these optional additional compound(s), and/or the amount thereof, such that the advantageous properties of the composition according to the invention are not, or are not substantially, adversely affected by the addition envisaged.

The compositions according to the invention are intended to be applied to the skin of the face and of the body, to mucous membranes and/or to keratin fibres such as the nails, the eyelashes or the hair.

They can be in any envisageable pharmaceutical form, such as a solid or soft oily gel, optionally comprising water; a solid or gelled oil-in-water, water-in-oil or multiple emulsion; a dispersion of oil in water; a multi-phase system and in particular a two-phase system. They can have the appearance of a cream, a salve, a soft paste, an ointment, a cast or moulded solid and in particular a stick.

They can be in particular in the form of a stick or a dish; and in particular in the form of a transparent anhydrous rigid gel, and more especially in the form of a translucent or transparent anhydrous stick.

The gelation of the oil is such that a rigid structure in the form of a tube or a stick can be obtained. When they are coloured, these tubes give, after application, a deposit of homogeneous colour.

These compositions find an application in particular as body hygiene compositions, for example in the form of deodorant sticks; as a hair composition, for example as a styling stick or a make-up stick for the hair; as a make-up composition for the skin of the face or the body or for mucous membranes, for example as a lipstick, a foundation cast as a stick or a dish, a face powder, an eyeshadow, a fixing base to be applied over a conventional lipstick, a concealer stick, a lip gloss, an eyeliner, a mascara or temporary tattoo products; as a care composition for the skin or mucous membranes, for example as a lipcare balm or base, an ointment for the body or a daily care cream; as an antisun composition or a self-tanning composition.

These compositions find a quite special application as transfer-resistant make-up or care compositions, in particular as lipsticks or foundations.

The invention is illustrated in greater detail in the examples which follow.

Method for Measuring the Hardness of the Sticks

The hardness is measured using a TA-XT2 texture analyser (from Rheo), at 22° C., using a smooth acrylic cone with an apex angle of 45°, and a total height which is greater than the penetration distance. The cone penetrates into the sample to a distance of 5 mm, at a speed of 2 mm/s. It is then kept immobile for 300 s, after which it is removed from the sample at a speed of 2 mm/s. The force exerted by the sample on the measuring body is recorded continuously. The maximum force is detected at the end of the penetration phase. This force value reflects the hardness of the sample.

Method for Measuring the Transparency or Translucency of the Sticks

The transparency or translucency is measured by measuring the transmittance, i.e. the percentage of light transmitted through a given sample, in the wavelength range corresponding to the visible range, i.e. between 400 nm and 900 nm.

This transmittance is measured continuously through a sample of thickened oil, placed in a glass cuvette with an optical path length of 1 cm, by difference with a sample termed the reference sample containing the same pure oil.

The measuring instrument is a Perkin-Elmer Lambda UV-Vis spectrophotometer.

The test composition (compound in oil) is heated until it is in the form of a homogeneous fluid, and is poured directly into the measuring cuvette. The cuvette is maintained at room temperature until its contents have cooled. The cuvette is then placed in the machine, the reference cuvette containing pure oil also being placed in the machine.

The transmittance is measured between 400 nm and 900 nm.

Standard Preparation of the Compounds

The compounds of formula (I) for which R=R' may be prepared according to the following 2 processes:

1) First Process:

The diamine and two equivalents of triethylamine are dissolved in 50 ml of tetrahydrofuran. Two equivalents of acyl chloride dissolved in THF are added and the reaction mixture is heated to the reflux point of the tetrahydrofuran, while monitoring the disappearance of the acyl chloride by infrared spectroscopy (most typically, two hours).

The solution is filtered from the precipitate, the organic phase is concentrated and a liquid/liquid extraction is performed on the solid compound obtained. The organic phase is subsequently dried and then concentrated, and the solid product obtained is recrystallized.

2) Second Process:

1 mol of diamine $H_2N—A—NH_2$ and 2 mol of tertiary amine such as triethylamine predissolved in the organic solvent S are added to a solution of 2 mol of acid chloride RCOCl in an organic solvent S such as toluene, chloroform or tetrahydrofuran. After addition, the reaction medium is refluxed for the time required for the acid chloride and the diamine to disappear (reaction time from about 2 hours to 24 hours). The addition of the reagents may also be reversed, i.e. the acid chloride may be added to a solution of diamine comprising the tertiary amine in the same relative proportions indicated above. The diamide formed is extracted from the reaction medium according to the extraction techniques that are well known to those skilled in the art.

EXAMPLE 1

A compound corresponding to formula (I), in which the two radicals R and R' represent a saturated linear chain containing 11 carbon atoms, the radical A is a saturated ring containing 6 carbon atoms and the radicals RCONH and RCONH' are in an ortho trans position, is prepared according to the process described above; this compound is trans-N,N'-bis(dodecanoyl)-1,2-diaminocyclohexane.

The following are mixed together with stirring, at room temperature:

200 mg of compound trans-N,N'-bis(dodecanoyl)-1,2-diaminocyclohexane and 10 ml of liquid paraffin sold under the name Parleam Oil by the company Nippon Oil Fats, i.e. a mixture containing 2% of compound.

The mixture is heated at 120° C. with stirring, until homogenized. It then becomes transparent, homogeneous and fluid. The homogeneous mixture is then allowed to cool slowly to room temperature.

A solid, hard translucent composition is thus obtained, which does not collapse outside the container, in the absence of any mechanical or thermal stimulation. This composition may be spread by simple pressure and allows a uniform, oily film to be obtained.

The hardness of the stick is measured, and the following result is obtained: 0.329 N.

The transparency of the stick is measured: the transmittance varies in a virtually linear continuous manner, from 3.7% at 400 nm to 38% at 900 nm (maximum value).

This clearly corresponds to a translucent composition.

EXAMPLE 2

The following are mixed together with stirring, at room temperature:

200 mg of compound prepared in Example 1, and 10 ml of tridecyl trimellitate fatty ester, i.e. a mixture containing 2% of compound.

The mixture is heated at 120° C. with stirring, until homogenized. It then becomes transparent, homogeneous and fluid. The homogeneous mixture is then allowed to cool slowly to room temperature.

A solid, hard translucent composition is thus obtained, which does not collapse outside the container, in the absence of any mechanical or thermal stimulation. This composition may be spread by simple pressure and allows a uniform, oily film to be obtained.

The hardness of the stick is measured, and the following result is obtained: 0.320 N.

The transparency of the stick is measured: the transmittance varies in a virtually linear continuous manner, from 12% at 400 nm to 45% at 900 nm (maximum value).

This clearly corresponds to a clear translucent, or even transparent, composition.

EXAMPLE 3

The following are mixed together with stirring, at room temperature:

200 mg of compound prepared in Example 1, and 10 ml of phenyl trimethicone fluid silicone oil sold under the name Dow Corning 556 Cosmetic Fluid by the company Dow Corning, i.e. a mixture containing 2% of compound.

The mixture is heated at 120° C. with stirring, until homogenized. It then becomes transparent, homogeneous and fluid. The homogeneous mixture is then allowed to cool slowly to room temperature.

A solid, hard transparent composition is thus obtained, which does not collapse outside the container, in the absence of any mechanical or thermal stimulation. This composition may be spread by simple pressure and allows a uniform, oily film to be obtained.

The hardness of the stick is measured, and the following result is obtained: 0.470 N.

The transparency of the stick is measured: the transmittance varies in a virtually linear continuous manner, from 34% at 400 nm to 78% at 900 nm (maximum value).

This clearly corresponds to a transparent composition.

EXAMPLE 4

250 mg of the compound of Example 1 are mixed with 5 ml of liquid paraffin (Parleam oil) and 25 mg of pigment (iron oxides), with stirring at room temperature. The mixture is heated at 120° C. until homogenized. It becomes transparent, coloured, homogeneous and fluid. The mixture is then allowed to cool slowly to room temperature.

A solid, coloured composition in the form of a stick is thus obtained. This composition does not show any separation of the pigment over time. It allows a uniform, oily film to be obtained. This composition may be used as a foundation or as a lipstick.

What is claimed is:

1. A cosmetic or pharmaceutical composition in solid form, comprising an oily phase and at least one compound of formula (I):

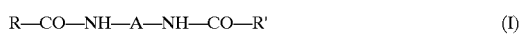  (I)

in which:
R and R', which may be identical or different, are chosen from a hydrogen atom and saturated and unsaturated, linear, branched and cyclic hydrocarbon-based chains containing from 1 to 22 carbon atoms, wherein said hydrocarbon-based chains may be substituted with at least one substituent chosen from —C$_6$H$_5$, —COOR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms, 1 to 4 halogen atoms, and 1 to 3 hydroxyl radicals, wherein said hydrocarbon-based chains may contain 1 to 3 hetero atoms chosen from O, S, and N, and with the proviso that both R and R' are not hydrogen atoms; and A represents a divalent radical chosen from saturated and unsaturated, linear, cyclic, and branched hydrocarbon-based chains containing 1 to 18 carbon atoms, wherein said hydrocarbon-based chains may be substituted with at least one substituent chosen from —C$_6$H$_5$, —COOR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms, 1 to 4 halogen atoms, and 1 to 3 hydroxyl radicals, wherein said hydrocarbon-based chains may contain 1 to 3 hetero atoms chosen from O, S, and N; and with the proviso that said composition may not comprise at least one wax in an amount greater than or equal to 5% by weight.

2. A composition according to claim 1, wherein A represents a divalent radical chosen from saturated and unsaturated, linear, branched, and cyclic hydrocarbon-based chains containing from 4 to 10 carbon atoms.

3. A composition according to claim 1, wherein A represents a divalent radical chosen from saturated cyclic hydrocarbon-based chains containing from 4 to 10 carbon atoms.

4. A composition according to claim 1, wherein A represents a divalent radical chosen from cyclohexylene, ethylene, propylene, dodecylene and methylphenylene radicals.

5. A composition according to claim 1, wherein R and R', which may be identical or different, are chosen from saturated and unsaturated, linear, branched and cyclic hydrocarbon-based chains containing from 6 to 18 carbon atoms.

6. A composition according to claim 1, wherein R and R', which may be identical or different, are chosen from saturated and unsaturated, linear, branched and cyclic hydrocarbon-based chains containing from 10 to 14 carbon atoms.

7. A composition according to claim 1, wherein R and R', which may be identical or different, are chosen from linear, saturated hydrocarbon-based chains containing from 10 to 14 carbon atoms.

8. A composition according to claim 1, wherein R and R', which may be identical or different, are chosen from saturated and unsaturated, linear, branched and cyclic hydrocarbon-based chains containing from 11 to 13 carbon atoms.

9. A composition according to claim 1, wherein R and R', which may be identical or different, are chosen from linear saturated hydrocarbon-based chains containing from 11 to 13 carbon atoms.

10. A composition according to claim 1, wherein at least one of R and R' is chosen from a linear saturated hydrocarbon-based chain containing 11 carbon atoms.

11. A composition according to claim 1, wherein R and R' are identical and are both not a hydrogen atom.

12. A cosmetic or pharmaceutical composition in solid form, comprising an oily phase and at least one compound of formula (I) below:

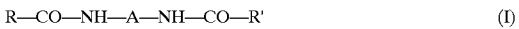  (I)

in which:
R and R', which may be identical or different, are chosen from a hydrogen atom and saturated and unsaturated, linear, branched and cyclic hydrocarbon-based chains containing from 10 to 16 carbon atoms, with the proviso that both R and R' are not hydrogen; and A represents a divalent radical chosen from saturated and unsaturated, non-aromatic, optionally branched hydrocarbon-based rings containing from 4 to 12 carbon atoms, wherein said hydrocarbon-based rings may be substituted with at least one substituent chosen from —C$_6$H$_5$, —COOR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms, halogen atoms, and hydroxyl radicals, and wherein said hydrocarbon-based rings may contain at least one hetero atom;

with the proviso that said composition may not comprise at least one wax in an amount greater than or equal to 5% by weight.

13. A composition according to claim 12, wherein A represents a divalent radical chosen from saturated and unsaturated, non-aromatic hydrocarbon-based rings containing from 5 to 7 carbon atoms.

14. A composition according to claim 13, wherein A represents a divalent radical chosen from saturated hydrocarbon-based rings containing from 4 to 12 carbon atoms.

15. A composition according to claim 12, wherein A represents a divalent radical chosen from saturated hydrocarbon-based rings containing from 5 to 7 carbon atoms.

16. A composition according to claim 12, wherein A represents a divalent radical chosen from cyclohexylene radicals.

17. A composition according to claim 12, wherein A represents a 1,2-cyclohexylene radical.

18. A composition according to claim 12, wherein R and R', which may be identical or different, are chosen from saturated and unsaturated, linear, branched and cyclic hydrocarbon-based chains containing from 10 to 14 carbon atoms.

19. A composition according to claim 12, wherein R and R', which may be identical or different, are chosen from saturated linear hydrocarbon-based chains containing from 10 to 16 carbon atoms.

20. A composition according to claim 12, wherein R and R', which may be identical or different, are chosen from saturated linear hydrocarbon-based chains containing from 10 to 14 carbon atoms.

21. A composition according to claim 12, wherein at least one of R and R' is chosen from linear saturated hydrocarbon-based chains containing 11 carbon atoms.

22. A composition according to claim 12, wherein R and R' are identical and are both not a hydrogen atom.

23. A cosmetic or pharmaceutical composition in solid form, comprising an oily phase and at least one compound of formula (I) below:

R—CO—NH—A—NH—CO—R'        (I)

in which:
R and R', which may be identical or different, are chosen from a hydrogen atom and saturated and unsaturated, linear, branched and cyclic hydrocarbon-based chains containing from 10 to 20 carbon atoms, with the proviso that both R and R' are not hydrogen atoms; and A represents a divalent radical chosen from saturated and unsaturated, linear, cyclic, and branched hydrocarbon-based chains containing 2 to 18 carbon atoms, wherein said hydrocarbon-based chains may be substituted with at least one substituent chosen from —$C_6H_5$, —COOR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms, halogen atoms, and hydroxyl radicals, wherein said hydrocarbon-based chains may contain at least one hetero atom;

with the proviso that said composition may not comprise at least one wax in an amount greater than or equal to 5% by weight.

24. A composition according to claim 23, wherein A represents a divalent radical chosen from saturated, linear and branched hydrocarbon-based chains containing from 3 to 12 carbon atoms.

25. A composition according to claim 23, wherein R and R', which may be identical or different, are chosen from saturated and unsaturated, linear, branched and cyclic hydrocarbon-based chains containing from 10 to 20 carbon atoms.

26. A composition according to claim 23, wherein R and R', which may be identical or different, are chosen from saturated and unsaturated, linear, branched and cyclic hydrocarbon-based chains containing from 11 to 18 carbon atoms.

27. A composition according to claim 23, wherein R and R', which may be identical or different, are chosen from saturated and unsaturated, linear, branched and cyclic hydrocarbon-based chains containing from 11 to 13 carbon atoms.

28. A composition according to claim 23, wherein R and R', which may be identical or different, are chosen from saturated linear hydrocarbon-based chains containing from 10 to 20 carbon atoms.

29. A composition according to claim 23, wherein R and R', which may be identical or different, are chosen from saturated linear hydrocarbon-based chains containing from 11 to 18 carbon atoms.

30. A composition according to claim 23, wherein R and R', which may be identical or different, are chosen from saturated linear hydrocarbon-based chain containing from 11 to 13 carbon atoms.

31. A composition according to claim 23, wherein at least one of R and R' is chosen from a saturated linear hydrocarbon-based chain containing from 11 carbon atoms.

32. A composition according to claim 23, wherein R and R' are identical and are both not a hydrogen atom.

33. A composition according to claim 12, wherein, in the at least one compound of (I):
A represents a divalent radical chosen from aryl and aralkyl rings containing from 6 to 12 carbon atoms, wherein
said rings may be substituted by at least one substituent chosen from —COOR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms, halogens and hydroxyl radicals;
and wherein said aryl and aralkyl rings may contain at least one hetero atom; and R and R', which may be identical or different, are chosen from a hydrogen atom and saturated and unsaturated, linear, branched, and cyclic hydrocarbon-based chains containing from 6 to 18 carbon atoms, with the proviso that both R and R' are not hydrogen.

34. A composition according to claim 33, wherein A represents a divalent radical chosen from aryl and aralkyl rings containing from 6 to 8 carbon atoms.

35. A composition according to claim 33, wherein R and R', which may be identical or different, are chosen from saturated and unsaturated, linear, branched and cyclic hydrocarbon-based chains containing from 10 to 16 carbon atoms.

36. A composition according to claim 33, wherein R and R', which may be identical or different, are chosen from saturated and unsaturated, linear, branched and cyclic hydrocarbon-based chains containing from 11 to 13 carbon atoms.

37. A composition according to claim 33, wherein R and R', which may be identical or different, are chosen from saturated linear hydrocarbon-based chains containing from 6 to 18 carbon atoms.

38. A composition according to claim 33, wherein R and R', which may be identical or different, are chosen from saturated linear hydrocarbon-based chains containing from 10 to 16 carbon atoms.

39. A composition according to claim 33, wherein R and R', which may be identical or different, are chosen from saturated linear hydrocarbon-based chains containing from 11 to 13 carbon atoms.

40. A composition according to claim 33, wherein R and R', which may be identical or different, are chosen from saturated linear hydrocarbon-based chains containing 11 carbon atoms.

41. A composition according to claim 3, wherein R and R' are identical and are both not a hydrogen atom.

42. A composition according to claim 1, in which the radical A represents a divalent radical chosen from ethylene, propylene, isopropylene, butylene, isobutylene, pentylene, hexylene, dodecylene and dodecanylene radicals.

43. A composition according to claim 1, in which A represents a divalent radical chosen from benzylene, phenylene, methylphenylene, bis-phenylene and naphthalene radicals.

44. A composition according to claim 1, in which the radicals R and R', which may be identical or different, are chosen from pentyl, hexyl, decyl, undecyl, dodecyl, pentadecyl, hexadecyl, heptadecyl, octadecyl, 3-dodecyloxypropionyl, 3-octadecyloxypropionyl, 3-dodecyloxypentyl, 3-octadecyloxypentyl and 11-hydroxyheptadecyl radicals.

45. A cosmetic or pharmaceutical composition in solid form, comprising an oily phase and at least one compound chosen from one of the following formulae:

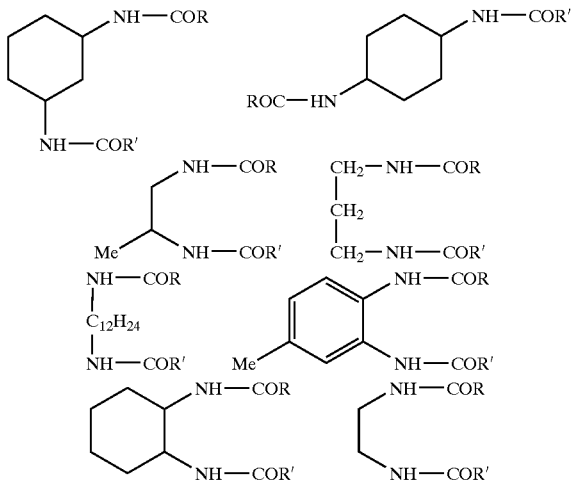

in which:
R and R', which may be identical or different, are chosen from a hydrogen atom and saturated and unsaturated, linear, branched and cyclic hydrocarbon-based chains containing from 1 to 22 carbon atoms, wherein said hydrocarbon-based chains may be substituted with at least one substituent chosen from —$C_6H_5$, —COR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms, 1 to 4 halogen atoms, and 1 to 3 hydroxyl radicals, wherein said hydrocarbon-based chains may contain 1 to 3 hetero atoms chosen from O, S, and N, with the proviso that both R and R' are not hydrogen atoms; and
with the proviso that said composition may not comprise at least one wax in an amount greater than or equal to 5% by weight.

46. A composition according to claim 45, wherein R and R', which may be identical or different, are chosen from saturated and unsaturated, linear, branched and cyclic hydrocarbon-based chains containing from 6 to 18 carbon atoms.

47. A composition according to claim 45, wherein R and R', which may be identical or different, are chosen from saturated and unsaturated, linear, branched and cyclic hydrocarbon-based chains containing from 10 to 14 carbon atoms.

48. A composition according to wherein R and R', which may be identical or different, are chosen from linear saturated hydrocarbon-based chains containing from 10 to 14 carbon atoms.

49. A composition according to claim 45, wherein R and R', which may be identical or different, are chosen from saturated and unsaturated, linear, branched and cyclic hydrocarbon-based chains containing from 11 to 13 carbon atoms.

50. A composition according to claim 45, wherein R and R', which may be identical or different, are chosen from linear saturated hydrocarbon-based chains containing from 11 to 13 carbon atoms.

51. A composition according to claim 45, wherein at least one of R and R' is chosen from linear saturated hydrocarbon-based chains containing 11 carbon atoms.

52. A composition according to claim 45, wherein R and R' are identical and are both not a hydrogen atom.

53. A composition according to claim 1, wherein the at least one compound of formula (I) is chosen from:
N,N'-bis(dodecanoyl)-1,2-diaminocyclohexane;
N,N'-bis(dodecanoyl)-1,3-diaminocyclohexane; and
N,N'-bis(dodecanoyl)-1,4-diaminocyclohexane.

54. A composition according to claim 1, wherein the at least one compound of formula (I) is chosen from:
N,N'-bis(dodecanoyl)-1,2-ethylenediamine;
N,N'-bis(dodecanoyl)-1-methyl-1,2-ethylenediamine; and
N,N'-bis(dodecanoyl)-1,3-diaminopropane,
N,N'-bis(dodecanoyl)-1,12-diaminododecane.

55. A composition according to claim 1, wherein the at least one compound of formula (I) is N,N'-bis(dodecanoyl)-3,4-diaminotoluene.

56. A composition according to claim 1, wherein the at least one compound of formula (I) is present in an amount ranging from 5% to 10%, relative to the total weight of the composition.

57. A composition according to claim 1, wherein the oily phase comprises at least one oil chosen from hydrocarbon-based, silicone and fluoro oils of animal, plant, mineral and synthetic origin.

58. A composition according to claim 1, wherein the oily phase comprises at least one oil chosen from hydrocarbon-based oils of animal origin, hydrocarbon-based plant oils, linear and branched hydrocarbons of mineral and synthetic origin, synthetic esters and ethers, hydroxylated esters, polyol esters, fatty alcohols containing from 12 to 26 carbon atoms, partially hydrocarbon-based and silicone-containing fluoro oils, volatile and non-volatile, linear and cyclic polymethylsiloxanes (PDMS), alkyldimethicones, silicones modified with at least one groups chosen from aliphatic, aromatic, and functional groups, wherein said aliphatic and aromatic groups may be fluorinated, and phenylsilicone oils.

59. A composition according to claim 1, in which the oily phase comprises at least one oil chosen from:
perhydrosqualene;
liquid triglycerides of fatty acids of 4 to 10 carbon atoms;
sunflower oil, corn oil, soybean oil, marrow oil, grapeseed oil, groundnut oil, sweet almond oil, beauty-leaf oil, palm oil, sesame oil, hazelnut oil, apricot oil, macadamia oil, castor oil, avocado oil; caprylic/capric acid triglycerides; jojoba oil, of karite butter;

liquid paraffins, petroleum jelly, polydecenes, purcellin oil, hydrogenated polyisobutene;

isopropyl myristate, 2-ethylhexyl palmitate, 2-octyldodecyl stearate, 2-octyldodecyl erucate, isostearyl isostearate, hydroxylated esters, propylene glycol dioctanoate, neopentyl glycol diheptanoate, diethylene glycol diisononanoate; pentaerythritol esters, tridecyl trimellitate;

octyldodecanol, 2-butyloctanol, 2-hexyldecanol, 2-undecylpentadecanol, oleyl alcohol;

polyphenylmethylsiloxanes, and phenyltrimethicones.

60. A composition according to claim 1, in which the oily phase comprises at least 50% by weight of volatile oils.

61. A composition according to claim 1, in which the oily phase comprises silicone oils.

62. A composition according to claim 1, having a hardness ranging from 0.04N to 3N.

63. A composition according to claim 1, wherein said composition comprises at least one wax in an amount greater than 0% and less than 5% by weight of wax, relative to the total weight of the composition.

64. A composition according to claim 1, wherein said composition comprises 0% by weight of at least one wax.

65. A composition according to claim 1, which has a maximum light transmittance value ranging from 2 to 100%, through a sample 1 cm thick, irrespective of the wavelength ranging from 400 and 800 nm.

66. A composition according to claim 1, further consisting essentially of at least one additive chosen from antioxidants, fragrances, dyes, essential oils, preserving agents, cosmetic active agents, vitamins, essential fatty acids, sphingolipids, self-tanning compounds, sunscreens, surfactants, polymers, pigments, nacres, fillers, and moisturizers.

67. A composition according to claim 1, in a form chosen from solid and soft oily gels, solid and gelled oil-in-water, water-in-oil, and multiple emulsions, dispersions of oil in water, multi-phase systems, creams, ointments, soft pastes, salves, cast and molded solids, and sticks.

68. A composition according to claim 1, which is a form chosen from deodorant sticks, styling sticks, make-up sticks for the hair, make-up compositions for the skin of the face and the body, lipsticks, foundations cast as a stick, foundations cast as a dish, face powders, eye shadows, fixing bases to be applied over a conventional lipstick, concealer sticks, lip glosses, eyeliners, mascaras, temporary tattoo products, care compositions for the skin, care compositions for mucous membranes, lip care balms and bases, ointments for the body, daily care creams, anti-sun compositions, and self-tanning compositions.

69. A composition according to claim 1, wherein said halogen atoms are fluorine.

70. A composition according to claim 45, wherein said halogen atoms are fluorine.

71. A composition according to claim 1, wherein said hydrocarbon-based chains contain 2 to 12 carbons.

72. A cosmetic or pharmaceutical composition in solid form, comprising an oily phase and at least one compound chosen from one of the following formulae:

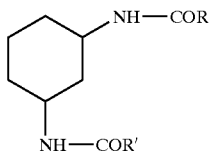
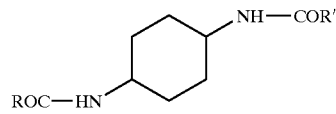
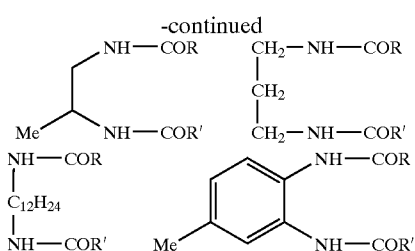

in which:

R and R', which may be identical or different, are chosen from a hydrogen atom and saturated and unsaturated, linear, branched and cyclic hydrocarbon-based chains containing from 1 to 22 carbon atoms, wherein said hydrocarbon-based chains may be substituted with at least one substituent chosen from —$C_6H_5$, —COOR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms, 1 to 4 halogen atoms, and 1 to 3 hydroxyl radicals, wherein said hydrocarbon-based chains may contain 1 to 3 hetero atoms chosen from O, S, and N, and with the proviso that both R and R' are not hydrogen atoms.

73. A composition according to claim 1, wherein the compounds of formula (I) are present in an amount ranging from 1 to 40% by weight, relative to the total weight of the composition.

74. A composition according to claim 1, wherein the compounds of formula (I) are present in an amount ranging from 2 to 15% by weight, relative to the total weight of the composition.

75. A composition according to claim 1, wherein the compounds of formula (I) are present in an amount ranging from 4 to 12% by weight, relative to the total weight of the composition.

76. A composition according to claim 58, wherein said aliphatic and aromatic groups are fluorinated.

77. A composition according to claim 58, wherein the silicones are modified with at least one functional group chosen from hydroxyl, thiol, and amine groups.

78. A composition according to claim 60, in which the oily phase comprises at least 75% by weight of volatile oils.

79. A composition according to claim 60, in which the oily phase comprises 100% by weight of volatile oils.

80. A composition according to claim 61, in which the silicone oils are in an amount ranging from 40–80% by weight of the oily phase.

81. A composition according to claim 61, in which the silicone oils are in an amount ranging from 60–75% by weight of the oily phase.

82. A composition according to claim 61, in which the oily phase comprises 100% of silicone oils.

83. A composition according to claim 62, which has a hardness ranging from 0.1 to 2.5N.

84. A composition according to claim 62, which has a hardness ranging from 0.2 to 2N.

85. A composition according to claim 63, comprising less than 2% by weight of wax, relative to the total weight of the composition.

86. A composition according to claim 63, comprising less than 0.5% by weight of wax, relative to the total weight of the composition.

87. A composition according to claim 65, which has a maximum light transmittance value of at least 50%, through a sample 1 cm thick, irrespective of the wavelength ranging from 400 and 800 nm.

88. A composition according to claim 67, wherein said solid and soft oily gels comprise water.

89. A cosmetic or pharmaceutical composition in solid form comprising an oily phase and at least one compound of formula (I) below:

R—CO—NH—A—NH—CO—R'  (I)

in which:

R and R', which may be identical or different, are chosen from a hydrogen atom and saturated and unsaturated, linear, branched and cyclic hydrocarbon-based chains containing from 1 to 22 carbon atoms, wherein said hydrocarbon-based chains may be substituted with at least one substituent chosen from —C$_6$H$_5$, —COOR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms), 1 to 4 halogen atoms, and 1 to 3 hydroxyl radicals, wherein said hydrocarbon-based chains may contain 1 to 3 hetero atoms chosen from O, S, and N, with the proviso that both R and R' are not hydrogen atoms; and A represents a divalent radical chosen from saturated and unsaturated, linear, cyclic, and branched hydrocarbon-based chains containing 1 to 18 carbon atoms, wherein said hydrocarbon-based chains may be substituted with at least one substituent chosen from —C$_6$H$_5$, —COOR" with R" being an alkyl group containing 2 to 12 carbon atoms, —CONHR" with R" being an alkyl group containing 2 to 12 carbon atoms, —OCONHR" with R" being an alkyl group containing 2 to 12 carbon atoms, —NHCONHR" with R" being an alkyl group containing 2 to 12 carbon atoms, 1 to 4 halogen atoms, and 1 to 3 hydroxyl radicals, wherein said hydrocarbon-based chains may contain 1 to 3 hetero atoms chosen from O, S, and N; and wherein said composition has a hardness ranging from 0.04N to 3N.

90. A composition according to claim 89, having a hardness ranging from 0.1 to 2.5N.

91. A composition according to claim 89, having a hardness ranging from 0.2 to 2N.

92. A composition according to claim 18, wherein R and R', which may be identical or different, are chosen from saturated linear hydrocarbon-based chains containing from 10 to 14 carbon atoms.

93. A composition according to claim 59, wherein said hydroxylated esters are chosen from isostearyl lactate, octyl hydroxystearate, octyldodecyl hydroxystearate, diisostearyl malate, triisocetyl citrate, hydroxylated fatty alkyl heptanoates, hydroxylated fatty alkyl octanoates, and hydroxylated fatty alkyl decanoates.

* * * * *

UNITED STATES PATENT AND TRADEMARK OFFICE
CERTIFICATE OF CORRECTION

PATENT NO. : 6,726,915 B2
DATED : April 27, 2004
INVENTOR(S) : Aude Livoreil et al.

It is certified that error appears in the above-identified patent and that said Letters Patent is hereby corrected as shown below:

Column 14,
Line 64, "claim 13," should read -- claim 12, --.

Column 16,
Line 16, "chain" should read -- chains --.

Column 17,
Line 5, "claim 3," should read -- claim 33, --.

Column 18,
Line 6, "to wherein" should read -- to claim 45, wherein --.
Line 33, delete "and".
Line 34, "N-N'-bis(dodecanoyl)-1,3-diaminopropane," should read -- N-N'-bis(dodecanoyl)-1,3-diaminopropane; and --.
Line 56, "groups" should read -- group --.

Column 21,
Line 25, "atoms)," should read -- atoms, --.

Signed and Sealed this

Thirteenth Day of July, 2004

JON W. DUDAS
*Acting Director of the United States Patent and Trademark Office*